US012370368B2

(12) United States Patent
Maldari

(10) Patent No.: US 12,370,368 B2
(45) Date of Patent: Jul. 29, 2025

(54) METHOD AND SYSTEM FOR COMMUNICATION BETWEEN A PLURALITY OF IMPLANTABLE MEDICAL DEVICES

(71) Applicant: SORIN CRM SAS, Clamart (FR)

(72) Inventor: Mirko Maldari, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 17/927,593

(22) PCT Filed: May 25, 2021

(86) PCT No.: PCT/EP2021/063930
§ 371 (c)(1),
(2) Date: Nov. 23, 2022

(87) PCT Pub. No.: WO2021/239741
PCT Pub. Date: Dec. 2, 2021

(65) Prior Publication Data
US 2023/0201604 A1    Jun. 29, 2023

(30) Foreign Application Priority Data

May 26, 2020  (FR) ...................................... 2005556

(51) Int. Cl.
*A61N 1/372*   (2006.01)
*A61B 5/00*    (2006.01)
(Continued)

(52) U.S. Cl.
CPC .......... *A61N 1/3627* (2013.01); *A61B 5/0024* (2013.01); *A61B 5/353* (2021.01); *A61N 1/37288* (2013.01)

(58) Field of Classification Search
None
See application file for complete search history.

(56) References Cited

U.S. PATENT DOCUMENTS 9,687,666 B2    6/2017  Jacobson
2018/0289973 A1  10/2018  Carney et al.
(Continued)

OTHER PUBLICATIONS

International Search Report and Written Opinion on PCT Appl. Ser. No. PCT/EP2021/063930 dated Jun. 29, 2021 (18 pages).

*Primary Examiner* — Erica S Lee

(57) ABSTRACT

A method of communication in a system comprising plurality of implantable medical devices, where a first device comprises a means for detection of a signal representative of atrial activity, a transmitter, and a controller, and a second device independent of the first device, the second device comprising a receiver and a controller. The method comprises synchronizing the first device with the second device, determining the duration of a cardiac cycle, determining a synchronization interval, the duration of the synchronization interval determined as a function of the duration of the cardiac cycle, the synchronization interval being shorter than the duration of the cardiac cycle, and the start of the synchronization interval is determined as a function of the synchronization signal, and activating the receiver of the second device during the synchronization interval, wherein the receiver of the second device is deactivated outside of the synchronization interval.

11 Claims, 8 Drawing Sheets

(51) Int. Cl.
    *A61B 5/353*     (2021.01)
    *A61N 1/362*     (2006.01)

(56)     References Cited

U.S. PATENT DOCUMENTS

| | | | |
|---|---|---|---|
| 2019/0143130 A1* | 5/2019 | Maile | A61B 5/0002 600/587 |
| 2019/0247666 A1 | 8/2019 | Ciciarelli et al. | |
| 2019/0296834 A1 | 9/2019 | Chin | |
| 2020/0368538 A1* | 11/2020 | Min | A61N 1/3756 |

* cited by examiner

METHOD AND SYSTEM FOR COMMUNICATION BETWEEN A PLURALITY OF IMPLANTABLE MEDICAL DEVICES

CROSS-REFERENCE TO RELATED PATENT APPLICATIONS

This application is a National Stage filing of International Application No. PCT/EP2021/063930, filed on May 25, 2021, which claims the benefit of and priority to French Patent Application No. 2005556, filed on May 26, 2020, the entire disclosure of which is hereby incorporated by reference herein.

BACKGROUND

The present invention relates to a method and a system for communication between a plurality of implantable medical devices.

Cardiac contractions ensure blood circulation. These contractions are produced by an electrical impulse called a stimulus. In a healthy heart, the stimulus originates in the sinus node located in the wall of the right atrium. From the sinus node, the stimulus travels first to the atria, which contract to force blood out of the atria into the resting ventricles and fill them.

In turn, after a delay called atrioventricular delay, the ventricles are excited by the stimulus and contract. This atrioventricular delay is essential for optimal function of the heart.

In patients with cardiac disorders, the origin of the stimulus and/or its pathway through the heart may be disrupted due to dysfunctions in the stimulus conduction system. This causes alterations in the heart rhythm, known as arrhythmias.

When the rhythm of the heart is too weak to meet the oxygenation needs of the body, it is called bradyarrhythmia.

In order to treat bradyarrhythmia, when drugs are not sufficient, it is known to resort to artificial pacing of the heart making use of implantable devices such as pacemakers. In particular, it is known to use a pacing system called double chamber pacemaker, which consists of a device that is implanted subcutaneously and which is connected to two leads that are used to deliver an artificial stimulus. The leads are implanted intravenously to join the right atrium and the right ventricle. When the leads are connected to the same implantable medical device such as a traditional pacemaker, synchronization between the leads can be achieved directly by the electronic circuitry of the implantable medical device. The use of intravenous leads does, however, present risks. Lead fracture is one of the most common causes of pacemaker malfunction. Removal of an implanted intravenous lead (or of a pacemaker) is a procedure with serious morbidity and high mortality, and is therefore, usually only carried out in cases of severe systemic infection that cannot be treated with antibiotics. In the majority of cases, fractured leads will be disconnected from the device and left in the heart. A new lead is then implanted next to the old one and connected to the automatic implantable defibrillator. However, this solution is only possible if there is still enough space in the vein, inasmuch as the presence of further leads can lead to a vein occlusion. As a consequence, the use of intracardiac leads is not ideally suited for young patients, who may require multiple leads over the course of their lives.

One solution to the problems associated with intracardiac leads, listed above, is to replace them with subcutaneous leads and/or autonomous pacemakers.

One of the main advantages of autonomous pacemakers is the absence of a housing and the reduction of foreign materials such as leads, which absence reduces the risk of infections.

However, autonomous pacemakers, can only be used for single chamber therapies, which limits the number of patients that are treatable.

SUMMARY

The present invention relates, in particular, to a pacemaker system comprising at least one autonomous leadless cardiac pacemaker. A leadless cardiac pacemaker consists of an energy source such as a battery unit, sensors, a current generator and a telemetry module. In particular, it is conceived to be implanted on the inside of the right ventricle and may be used as an alternative to implantable single chamber pacemakers.

To increase the percentage of the population that can benefit from an autonomous pacemaker, one solution is to have a system of a plurality of implantable medical devices, where a wireless communication between the devices is required in order to send and receive physiological information such as the detection of PQRST complex waves. This information is, in particular, required in order to provide synchronized therapy. Thus, a synchronization signal representing the detection of a PQRST complex wave may be sent by a device implanted in one chamber to synchronize the therapy of another device implanted in another chamber.

However, wireless methods of communication for implantable medical devices, such as radio frequency, intrabody communication (IBC) and inductive coupling, are energy hogs and reduce battery life.

The problem is all the more critical for the device that is configured to receive the synchronization signal inasmuch as it requires that the receiving means of the device remain activated while awaiting a signal to be received, further reducing the capacity of the battery.

Therefore, it is a task of the present invention to improve the wireless communication of such implantable device systems in order to reduce their power consumption and thereby extend their life.

The task of the present invention is achieved by a method of communication in a system comprising a plurality of implantable medical devices, wherein a first device comprises at least one means for detection of a signal that is representative of atrial activity, a transmitter means, and a controller configured to analyze a signal representative of the atrial activity, and a second device, that is independent of the first implantable medical device, comprising at least one receiving means and a controller. The method comprises: A) a step for time synchronization of the first device with the second device, by sending a synchronization signal from the transmitter means of the first device to the second device, the synchronization signal being sent following the identification, by means of the controller of the first device, of a predefined electrical wave of the PQRS complex of a signal representative of the atrial activity, B) a step for determination of the duration of a cardiac cycle. Steps A and B being followed by: C) a step for determination of a synchronization interval, the duration of which synchronization interval is determined as a function of the duration of the cardiac cycle so as to be shorter than the duration of the cardiac cycle, and the start of which synchronization interval is determined as a function of the synchronization signal, D) a step for activation of the receiving means of the second device during the synchronization interval, wherein the receiving means of the second device is deactivated outside of the synchronization interval by the controller of the second device.

The method of communication is improved because the receiving means of the second device is not continuously activated, but rather only for a time interval shorter than the duration of a cardiac cycle.

The partial activation of the receiving means of the second device during each cardiac cycle is sufficient for the purpose of synchronization of the system, inasmuch as the synchronization interval takes into consideration the time marker which is related to the detection of one of the electrical waves of the PQRS complex. The detection of one of the electrical waves of the PQRS complex permits the identification of a cardiac event. The synchronization interval is therefore determined according to physiological information that is useful for the synchronization of the system and related to the cardiac rhythm of the patient. The synchronization interval is therefore advantageously adjusted according to the physiological characteristics of the patient.

The present method thus makes it possible to reduce the time period during which the receiving means of the second device must be activated to allow wireless communication to take place. As a consequence, it is made possible to save on the power requirements of the second device and thus extend its lifetime.

The present invention, related to a method of communication, can be further improved thanks to the following embodiments.

According to one embodiment, for one cardiac cycle, a first time marker marking the sending of the synchronization signal by the transmitter means of the first device may be determined, and a second time marker marking the receipt of the synchronization signal by the receiving means of the second device may be determined, and the synchronization interval of the first device for a subsequent cardiac cycle may be determined as a function of the first time marker, the synchronization interval of the second device for a subsequent cardiac cycle may be determined as a function of the second time marker.

Thus, the synchronization interval of the second device is a function of the second time marker which is itself related to a physiological characteristic of the patient, such as the P wave, wherein the P wave is one of the electrical waves of the PQRST complex.

According to one embodiment, during the synchronization interval of the second device, the receiving means of the second device may be activated during a plurality of predefined activation time slots and may be deactivated during a plurality of predefined deactivation time slots, the plurality of predefined activation time slots of the second device being distributed over the synchronization interval of the second device so as to be synchronized with signal pulse slots of the first device as a function of the first time marker and the second time marker.

Thus, the power consumption of the receiving means of the second device can be further advantageously reduced because the receiving means is not activated over the entire synchronization interval but only on a slot by slot basis. This does not in any way interfere with the receipt of a synchronization signal since the activation slots are advantageously adjusted in relation to the first time marker, which marks the sending of the synchronization signal by the first device.

According to one embodiment, the transmitter means of the first device may be configured to send a single synchronization signal per cardiac cycle.

Thus, the method of communication does not require that a series of pulses is transmitted by the first device. In effect, the present method allows the single synchronization signal sent by the first device to "fall" within an activation time slot of the receiving means of the second device due to the synchronization of the first and second time markers.

According to one embodiment, each of the predefined activation time slots may be of the same duration and each of the predefined deactivation time slots may be of the same duration and each of the predefined activation and deactivation time slots may alternatingly succeed each other in the synchronization interval.

The succession of the activation and deactivation time slots is thus periodic, further promoting the likelihood that a synchronization signal will be received during the synchronization interval.

According to one embodiment, the duration of an activation time slot may be shorter than or equal to the duration of a deactivation time slot.

Thus, the power consumption of the receiving means of the second device may be further reduced.

According to one embodiment, the duration of an activation time slot may represent between 0.3 and 50% of the duration of a deactivation time slot, in particular 5 to 10%.

Thus, the power consumption of the receiving means of the second device may be reduced as much as possible.

According to one embodiment, the duration of a pulse during which the transmitter means of the first device can be configured to transmit a synchronization signal corresponds to 25 to 80% of the duration of an activation time slot, in particular 50%.

Thus, the activation time slots that correspond to the time slots during which the receiving means of the second device is activated to "listen" and detect a synchronization signal are longer than the duration of transmission of a synchronization signal. Thus, there is a greater chance that receipt of the synchronization signal will occur during an activation time slot of the second device.

According to one embodiment, the first time marker may mark the start or end of the sending of the synchronization signal or a predetermined time during the sending of the synchronization signal.

The adjustment of the synchronization interval for the second device with that of the first device can thus be improved, as the "timing" of the first time marker is defined with more precision.

According to one embodiment, in step A), the predefined electrical wave detected by means of the controller of the first device may correspond to the P wave of the PQRS complex.

The detection of the P wave is particularly suitable since it marks the depolarization during the contraction of the atria and thus constitutes physiologically relevant information for the atrioventricular delay and synchronization.

According to one embodiment, in step A), the predefined electrical wave may be detected by means of the controller of the first device by the analysis of an electrogram, an electrocardiogram, of data measured by an accelerometer, of data measured by cardiographic impedance or of data measured by an acoustic sensor.

The method can thus advantageously be implemented with different detection means.

According to one embodiment, over at least two successive cardiac cycles, the first device and the second device can communicate with each other in an asynchronous manner during steps A and B and the receiving means of the second device is activated in a continuous manner during the at least two successive cardiac cycles.

Thus, the first device and the second device are configured to each independently determine a time marker in order to determine and adjust the synchronization interval.

According to one embodiment, the controller of the second device may be configured to deactivate the receiving means of the second device during the remaining time of the synchronization interval of the second device after receipt of the synchronization signal.

Thus, the power consumption of the receiving means of the second device may be reduced as much as possible.

According to one embodiment, the controller of the second device may be configured to send an alert signal through a transmitter means of the second device to a receiving means of the first device when a synchronization signal is not received by the second device during the synchronization interval of the second device.

Thus, the first device is alerted that the second device, configured to be implanted in the right ventricle, has not received the information relating to the detection of the predefined electrical wave. The first device having sent the synchronization signal (which has not been received by the second device), the first device is able to see that the signal has been lost during its journey. Local pacing of the right atrium may then be necessary.

The task of the present invention is also achieved by a system of a plurality of implantable medical devices. The system comprises a first device comprising at least one detection means, a transmitter means, and a controller configured to analyze a signal representative of the atrial activity. The system comprises a second device, independent of the first implantable medical device, comprising at least one receiving means and a controller. The receiving means of the second device is configured to be activated and deactivated by the controller of the second device. The controller of the first device and the controller of the second device are configured to implement the method according to the embodiments described above.

Thus, the multi-implantable device system is improved since the receiving means of the second device is not continuously activated, but rather only during a synchronization interval that is shorter than the duration of one cardiac cycle.

The partial activation of the receiving means of the second device during each cardiac cycle is sufficient for the purposes of synchronization of the system, inasmuch as the synchronization interval takes into consideration the time marker that is related to the detection of one of the electrical waves of the PQRS complex. The detection of one of the electrical waves of the PQRS complex enables the identification of a cardiac event. The synchronization interval is therefore determined as a function of physiological information that is useful for the synchronization of the system and related to the cardiac rhythm of the patient. The synchronization interval is therefore advantageously adjusted according to physiological characteristics of the patient.

According to one embodiment, the first implantable medical device may be an implantable subcutaneous medical device, an event loop recorder or a leadless pacemaker, and the second medical device may be a leadless pacemaker.

The system is thus suitable for dual-chamber synchronization therapy. In particular, the system is suitable for dual-chamber synchronization therapy with an implantable leadless pacemaker in the right atrium and an implantable leadless pacemaker in the right ventricle.

BRIEF DESCRIPTION OF THE FIGURES

The invention and its advantages will be elucidated in more detail in the following by means of preferred embodiments and with particular reference to the following accompanying figures, wherein.

DETAILED DESCRIPTION

The invention will now be described in more detail using advantageous embodiments by way of example and with reference to the figures. The embodiments described are simply possible configurations and it should be kept in mind that the individual characteristics as described above may be provided independently of each other or may be omitted altogether when implementing the present invention.

The present invention relates to a method of communication for a system of a plurality of implantable medical devices, as well as to such a system.

Embodiments of such a system of a plurality of implantable medical devices are first described with reference to FIGS. 1, 3 and 4.

The method of communication according to the present invention that can be implemented by a system of a plurality of implantable medical devices is then described with reference to FIGS. 5 through 10.

Figure 1:
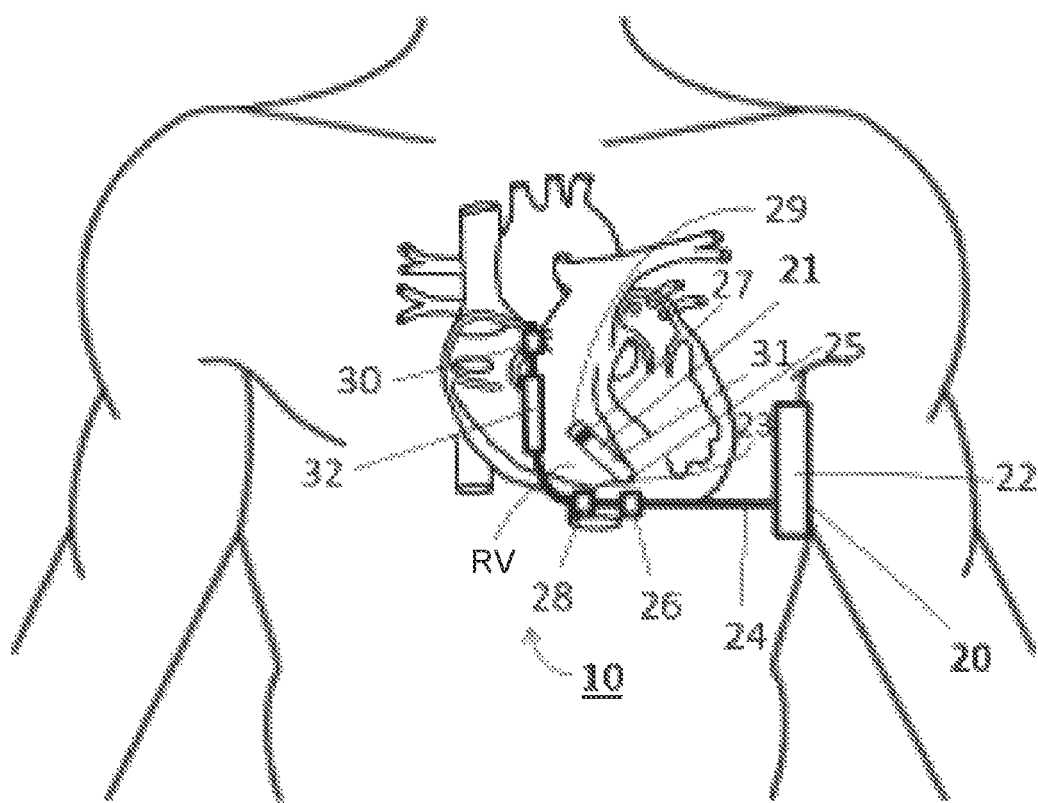
FIG. 1 represents a multi-device system 10 according to a first embodiment of the present invention.

FIG. 1 represents a multi-device system 10 according to a first embodiment of the present invention comprising two implantable devices 20, 21.

The multi-device system 10 represented in FIG. 1 comprises a subcutaneous implantable device 20 and a leadless autonomous pacemaker 21 implanted in the right ventricle RV.

The subcutaneous implantable device 20 represented in FIG. 1 comprises a housing 22 and a subcutaneous lead 24 provided with three electrodes 26, 28, 30 and a defibrillation electrode 32. Although not visible in FIG. 1, the housing 22 comprises a transmitter means, such as a radio frequency (RF) transmitter device or uses an intra-body communication connection, and a controller. The housing 22 may also comprise a receiving means.

In one variant, an event recorder or an implantable loop recorder comprising at least a pair of electrodes may be used in the stead of the subcutaneous implantable device 20.

The subcutaneous implantable device 20 is configured to detect the atrial activity using any one of the methods known in the state of the art, by way of example, by an electrocardiogram (ECG), by impedance cardiography, by an acoustic sensor, and/or by an accelerometer.

Figure 2:
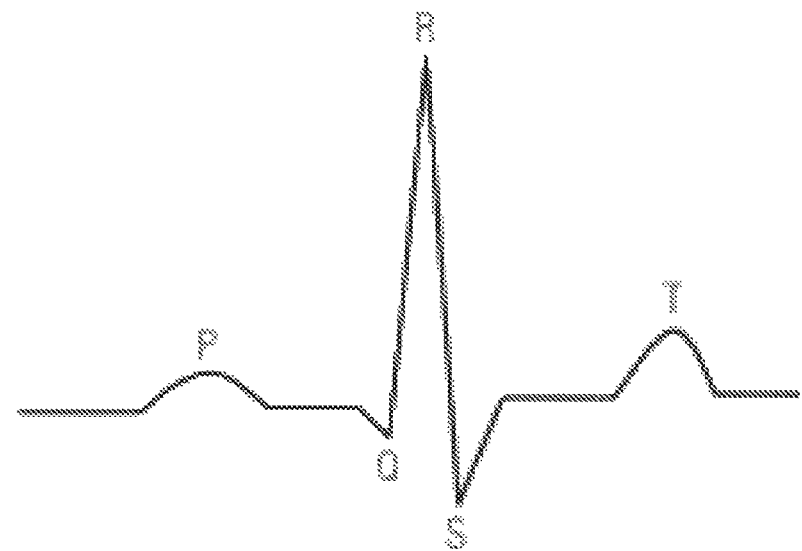
FIG. 2 schematically represents a standard plot of a PQRST complex.

In the first embodiment of the invention, the subcutaneous implantable device 20 is configured to analyze data representative of an ECG. The analysis of the data representative of an ECG makes it possible to detect at least one of the five P, Q, R, S, T waves of the PQRST complex which are electrophysiological characteristics. An example of a PQRST complex is shown in FIG. 2. The subcutaneous implantable device 20 is, in particular, configured to identify a time marker corresponding to the detection of an electrical wave of the PQRST complex. The detection of the P wave is preferred inasmuch as it marks the depolarization of the atria and thus constitutes physiologically relevant information for the atrioventricular delay and synchronization.

Detection of the P wave can, for example, be determined by identifying a local maximum.

The leadless autonomous pacemaker 21 comprises a tip electrode 23 arranged at a distal end 25 of the device 21, and a ring electrode 27 arranged toward a proximal end 29 of the device 21. The electrodes 23, 27 may form a receiver dipole or a transmitter dipole. It should be noted that the present invention is not limited to the use of a tip electrode and a ring-type electrode but may be implemented using any type of electrode comprised in a leadless autonomous pacemaker.

The tip electrode 23 may be a detection electrode or a pacing electrode. In one variant, the electrode 23 is both a detection electrode and a pacing electrode.

Although not visible in FIG. 1, the body 31 of the leadless autonomous pacemaker 21 may encapsulate a battery unit, a controller, and a receiving means, such as an RF receiving device or use an intra-body communication connection. The body 31 may also comprise a transmitter means.

The receiving means of the leadless autonomous pacemaker 21 is configured to communicate wirelessly with the transmitter means of the subcutaneous implantable device 20, in particular by means of an intra-body communication connection.

The subcutaneous implantable device 21 may be configured to detect cardiac activity making use of any one of the methods known in the state of the art, for example, by an electrocardiogram (ECG), an electrogram (EGM), by impedance cardiography, by an acoustic sensor, and/or by an accelerometer.

In one variant, the wireless communication between the devices 20, 21 could likewise also be achieved making use of other wireless methods of communication such as intra-body communication or inductive coupling.

In the system 10, the leadless autonomous pacemaker 21 is thus configured to receive a signal sent from the subcutaneous implantable device 20. In particular, this may be a synchronization signal containing timing information related to an atrial depolarization. Such a synchronization signal may enable synchronization of the contractions of the ventricle. The synchronization signal may be used to deliver pacing to the right ventricle based on the physiological heart activity of the patient that is detected by the subcutaneous implantable device 20.

Figure 3:
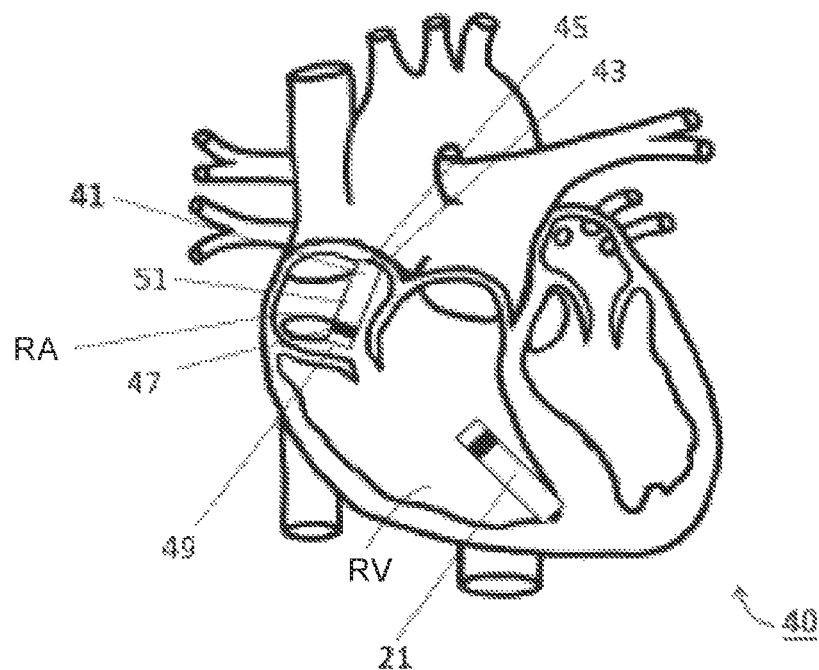
FIG. 3 represents a multi-device system 40 according to a second embodiment of the present invention.

FIG. 3 illustrates a multi-device system 40 according to a second embodiment of the present invention comprising two implantable devices 21, 41.

The elements with the same numerical references already used for the description of FIG. 1 will not be described again in detail, and reference is made to their descriptions above.

The implantable device 21 corresponds to the leadless autonomous pacemaker 21 already described in reference to FIG. 1 and to which reference is made.

In the second embodiment, a second leadless autonomous pacemaker 41 is used in the stead of the subcutaneous implantable medical device 20 of the first embodiment.

As illustrated in FIG. 3, the leadless autonomous pacemaker 41 is configured to be implanted in the right atrium (RA).

The autonomous leadless pacemaker 41 is configured to detect atrial activity using any of the methods known in the state of the art, for example, by an electrocardiogram (ECG), by an electrogram (EGM), by impedance cardiography, by an acoustic sensor, and/or by an accelerometer.

The leadless autonomous pacemaker 41 is configured to analyze data that are representative of an ECG. The analysis of data that are representative of an ECG makes detection possible of at least one of the five P, Q, R, S, T waves of the PQRST complex as known in the prior art. An example of a PQRST complex is illustrated in FIG. 2. The leadless autonomous pacemaker 41 is, in particular configured to identify a time marker corresponding to the detection of an electrical wave of the PQRST complex.

In a similar manner to the leadless autonomous pacemaker 21, the leadless autonomous pacemaker 41 comprises a tip electrode 43 arranged at a distal end 45 of the pacemaker 41, and a ring electrode 47 arranged toward a proximal end 49 of the pacemaker 41. The electrodes 43, 47 may form a receiver dipole or a transmitter dipole. It should be noted that the present invention is not limited to the use of a tip electrode and a ring-type electrode but may be implemented using any type of electrode comprised in a leadless autonomous pacemaker.

The tip electrode 43 may be a detection electrode or a pacing electrode. In one variant, the electrode 43 is both a detection electrode and a pacing electrode.

Although not visible in FIG. 3, the body 51 of the leadless autonomous pacemaker 41 may encapsulate a battery unit, a processor, a controller, and a transmitter means, such as an RF transmitter device. The body 51 may also include a receiving means.

The transmitter means of the leadless standalone pacemaker 41 is configured to communicate wirelessly with the receiving means of the leadless standalone pacemaker 21, in particular by means of an intra-body communication connection.

In one variant, the wireless communication between the devices 21, 41 could also occur by means of other wireless methods of communications such as intra-body communication or inductive coupling.

In one embodiment that is not shown, a system according to the present invention comprises a subcutaneous implantable device 20 and two leadless pacemakers 21, 41.

Figure 4:
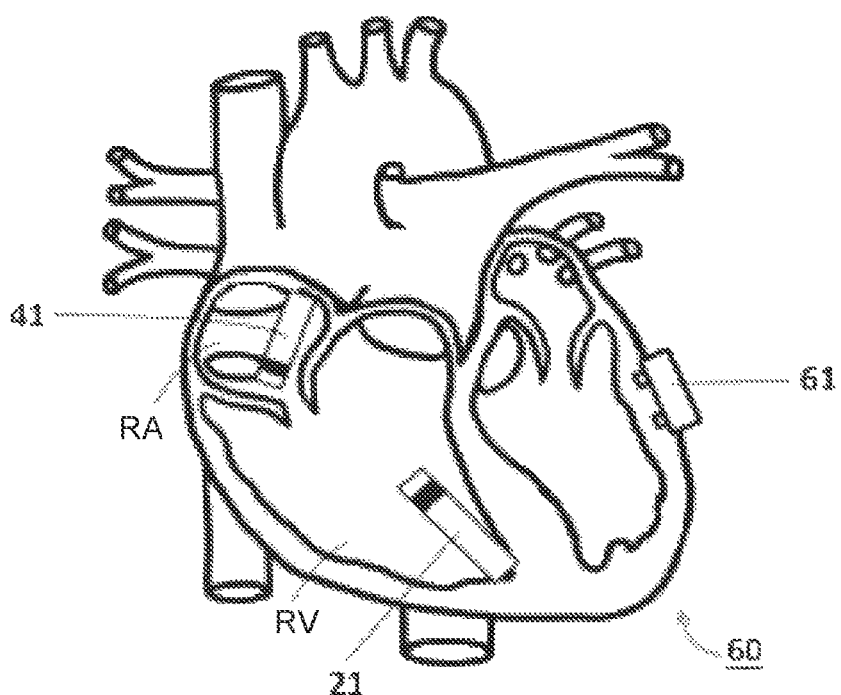
FIG. 4 represents a multi-device system 60 according to a third embodiment of the present invention.

FIG. 4 illustrates a multi-device system 60 according to a third embodiment of the present invention comprising three implantable devices 21, 41, 61.

Elements with the same numerical references already used for the description of FIGS. 1 and 3 will not be described again in detail, and reference is made to their descriptions above.

When compared to the second embodiment, the multi-device system 60 of the third embodiment comprises a third implantable medical device 61. The multi-device system 60 is of the so-called triple-chamber resynchronization system type, also referred to as "CRT-P" for "Cardiac Resynchronization Therapy-Pacemaker."

The implantable devices 21, 41 correspond respectively to the leadless autonomous pacemakers 21, 41 already described in reference to FIGS. 1 and 3 and to which reference is made.

The third device 61 is a leadless autonomous pacemaker 61 implanted in an epicardial manner on the myocardial wall.

In each of the embodiments of the present invention described in reference to FIGS. 1, 3 and 4, the implantable devices 20, 21, 41, 61 may contain both receiving means and transmitter means, particularly suitable for RF communication. Thus, each of the implantable devices 20, 21, 41, 61 is configured both to send a signal and to receive a signal in order to enable wireless communication in each of the systems 10, 40, 60.

Moreover, each of the implantable devices 20, 21 and 41 are capable of determining the duration of a cardiac cycle.

The wireless method of communication according to the present invention relates to the synchronization of at least two implantable devices such as 20, 21, 41, 61 comprised in a system such as systems 10, 40 or 60. The wireless method of communication according to the present invention is hereinafter described. The systems 10, 40, 60 are each configured to implement said method of communication. In particular, the method of communication is hereinafter described for a system comprising a first device and a second device.

Figure 5:
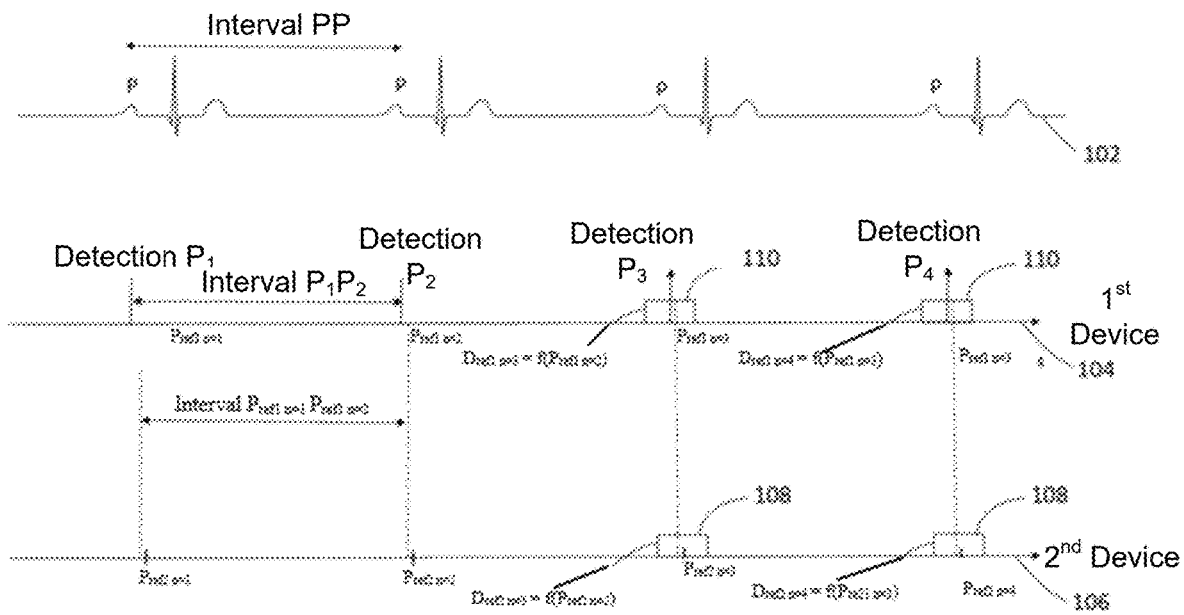
FIG. 5 represents a diagram that schematically illustrates the method of communication according to a first embodiment of the present invention.

FIG. 5 schematically illustrates the operation of the method of communication according to a first embodiment of the present invention.

FIG. 5 shows three time axes 102, 104, 106. The unit of the axes 102, 104, 106 is expressed in milliseconds (ms).

An ECG is represented on the time axis 102. The ECG illustrated on the time axis 102 comprises a plurality of PQRST complex for each of the cardiac cycles depicted. The duration of a complete cardiac cycle can be determined as the time between two successive identical waves. In FIG. 5, the duration of the cardiac cycle is represented by the interval PP, illustrated between the two local maximums representing the P wave of the cardiac cycle. Four successive cardiac cycles, n=1 to n=4, are annotated in FIG. 5.

The interval PP is representative of the duration of a complete cardiac cycle, and typically lasts approximately one second or more.

A first device is configured to analyze the ECG 102 and to determine a characteristic of the ECG in order to identify a wave of the PQRS complex, in particular the P wave. The characteristic may be, for example, the local maximum assigned to the P wave. The first device may also be configured to record the ECG 102.

The first device is configured to determine the duration of a cardiac cycle. This first device may be the subcutaneous implantable device 20, a recorder, or the leadless autonomous pacemaker 41 configured to be implanted in the right atrium (RA). The first device in FIG. 5 comprises at least one transmitter means, for example, by means of an intra-body communication connection.

Detections of the P wave for each PP cycle (see "detection $P_1$" to "detection $P_4$") identified by the first device are represented on the time axis 104.

The time axis 106 refers to a second device of a multi-device system, as described with reference to FIGS. 1, 3 and 4. This second device may be the leadless autonomous pacemaker 21 configured to be implanted in the right ventricle (RV). The second device may be configured to determine the duration of a cardiac cycle. The second device may thus be capable of delivering ventricular pacing.

The second device of FIG. 5 is independent of the first implantable medical device and comprises at least one receiving means.

The method of the present invention is a method of wireless communication between said first device and said second device constituting a multi-device system in order to allow synchronization of the devices with each other. Said method is hereinafter described.

Firstly, let us consider the first cardiac cycle n=1 illustrated in FIG. 5, during which the first and second devices are not yet synchronized.

As explained above, the first device is configured to analyze the ECG and detect a P wave. During the first cardiac cycle n=1, a P wave is detected by the first device and is annotated "detection $P_1$" on the time axis 104.

Following the detection and identification of the $P_1$ wave, the transmitter means of the first device is configured to send a synchronization signal to the second device. The time marker $P_{ref1\ n=1}$ on the time axis 104 corresponds to the time marker that marks the sending of the synchronization signal for the first cardiac cycle illustrated in FIG. 5.

This synchronization signal is received by the receiving means of the second device and is indicated by the time marker $P_{rep\ n=1}$ on the time axis 106.

Then, during the next cardiac cycle n=2, a P wave is once again detected and identified by the first device and is annotated "detection $P_2$" on the time axis 104.

Following the detection and identification of the $P_2$ wave, the transmitter means of the first device is configured to send a synchronization signal to the second device. The $P_{ref1\ n=2}$ time marker on the time axis 104 corresponds to the time marker that marks the sending of the synchronization signal for the second cardiac cycle n=2 illustrated in FIG. 5.

This synchronization signal is received by the receiving means of the second device and is indicated by the time marker $P_{ref2\ n=2}$ on the time axis 106.

According to the present invention, the duration of the first cardiac cycle n=1 is determined between $P_{ref1\ n=1}$ and $P_{ref1\ n=2}$ (see "$P_{ref1\ n=1}$ $P_{ref1\ n=2}$ interval" in FIG. 5). This allows to refer to a reference that is common to the first and second devices.

In one variant, the duration between "detection $P_1$" and "detection $P_2$" may allow determination of the duration of the first cardiac cycle n=1 (see "interval $P_1P_2$" in FIG. 5).

Then, during the next cardiac cycle n=3, a P wave is once again detected and identified by the first device and is annotated "detection $P_3$" on the time axis 104.

Following the detection and identification of the $P_3$ wave, the transmitter means of the first device is configured to send a synchronization signal to the second device. The time marker $P_{ref1\ n=3}$ on the time axis 104 corresponds to the time marker that marks the sending of the synchronization signal for the third cardiac cycle illustrated in FIG. 5.

This synchronization signal is received by the receiving means of the second device and is indicated by the time marker $P_{ref2\ n=3}$ on the time axis 106.

According to the present invention, and by analogy with the first cycle, the duration of the second cardiac cycle n=2 is determined between $P_{ref1\ n=2}$ and $P_{ref1\ n=3}$.

In one variant, the duration between "detection $P_2$" and "detection $P_3$" allows for the determination of the duration of the second cardiac cycle n+2.

A synchronization interval 108 for the second device may be determined for the third cardiac cycle n=3 starting from the time marker $P_{ref2\ n=2}$ and the duration of the second cardiac cycle. This synchronization interval 108 corresponds to a listening window, which is to say, the receiving means of the second device is activated over the synchronization interval 108 for the purpose of receiving a synchronization signal transmitted by the first device. A signal or message may thus be received by the receiving means of the second device during the synchronization interval 108.

The duration of the synchronization interval 108 is determined in such a manner to be shorter than the duration of the second cardiac cycle. The synchronization interval 108 may be less than 0.8 s in duration, in particular, less than 0.4 seconds.

The start of the synchronization interval 108, indicated by the reference $D_{ref2\ n=3}$ is determined as a function of the time marker $P_{ref2\ n=2}$ of the preceding cardiac cycle n+2.

Since the synchronization interval 108 is a function of the time marker $P_{ref2\ n=2}$ of the previous cardiac cycle n+2, this allows the synchronization interval 108 to be arranged over the third cycle such that the receipt of the synchronization signal occurs during said synchronization interval 108.

The receipt of the synchronization signal is indicated by the time marker $P_{ref2\ n=3}$.

The determination of the start $D_{ref2\ n=3}$ and the duration of the synchronization interval 108 over the third cardiac cycle notably takes into consideration, the maximum acceleration between beats, which generally does not exceed 10 to 40%, in particular 25 to 35% of the duration of a cardiac cycle.

Moreover, the determination of the synchronization interval 108 also takes into account the time it takes the myocardium to respond to atrial activity. This is a parameter that can be programmed by a physician to improve the physiological response of the heart. This parameter may correspond to 0-50%, in particular 0-30%, of the duration of a cardiac cycle.

According to the present invention, the receiving means of the second device is activated during the synchronization interval 108 and is deactivated outside the synchronization interval 108 by the controller of the second device.

Thus, the receiving means of the second device is not continuously activated for the duration of a complete cardiac cycle, which allows to reduce the power consumption of the second device. Indeed, as long as the receiving means of the second device is activated, it consumes power. By activating the receiving means during the synchronization interval 108 rather than over the duration of a complete cardiac cycle, the power consumption required for wireless communication for the purpose of resynchronization can be reduced since the duration of powering up of the receiving means is limited to the duration of the synchronization interval 108.

This is not, however, a matter of turning off all functionalities of the second device all at once, which second device implements other functions such as detection, timing or pacing in parallel with the functionality of the receiving means.

A synchronization interval 110 for the first device may likewise be determined starting from the time marker $P_{ref1\ n=2}$ and the duration of the second cardiac cycle. The start of the synchronization interval 110 for the third cardiac cycle n+3 is indicated by the time marker $D_{ref1\ n=3}$. The start of the synchronization interval 110 $D_{ref1\ n=3}$ is thus determined, in particular, as a function of the time marker $P_{ref1\ n=2}$.

The synchronization interval 110 for the first device corresponds to a sending window, which is to say, an interval during which the synchronization signal is likely to be sent, according to the identification of a P wave. For the third cardiac cycle n+3, the sending of the synchronization signal is indicated by the time marker $P_{ref1\ n=3}$.

The determination of the synchronization intervals 108, 110 for the fourth and subsequent cardiac cycles n+4 (which are not shown in FIG. 5) is carried out in the same manner as explained above for the third cardiac cycle.

An advantage of the present method is that the communication intervals 108, 110 are adjusted over time as a function of a cardiac event (the detection of a P wave) and are thus tailored to the physiological characteristics of a patient.

In an alternative that is not shown, the synchronization interval 110 may be arranged over the third cycle n+3 as a function of the time marker $P_{ref1\ n=2}$ and the duration of the second cardiac cycle in such a manner that the detection of the P wave is not comprised in the synchronization interval 110. In this case, the synchronization interval 110 is shifted to the right of the time axis 104 relative to the first embodiment. In this alternative, the synchronization interval 108 is thus also shifted to the right of the time axis 104 relative to the first embodiment. This alternative is particularly suitable for sending a synchronization message containing a data set.

Let us note that the first device may send a synchronization "signal" or "message." In the present description, a synchronization "signal" refers to a signal comprising information encoded on a single bit whereas a synchronization "message" refers to a signal comprising information encoded on multiple bits.

The difference between a synchronization "signal" and a synchronization "message" is thus related to the way the timing information of the P wave detection is encoded.

In a synchronization message, the timing of the P wave detection is encoded and thus allows more detailed information to be sent to the second device.

In a synchronization signal, the timing information of the P wave detection is implicit in the timing of the sending of said signal. Thus, a signal comprising information coded on a single bit can be sent.

The time markers $P_{ref1}$ and $P_{ref2}$ for each cycle n serve as time references to synchronize the synchronization intervals 108, 110 with each other. In particular, the time markers $P_{ref1}$ and $P_{ref2}$ are used, in particular, to ensure that the synchronization intervals 108, 110 overlap or even align.

Thus, the time marker $P_{ref2}$ is used to adjust the activation of the receiving means of the second device.

Figure 6:
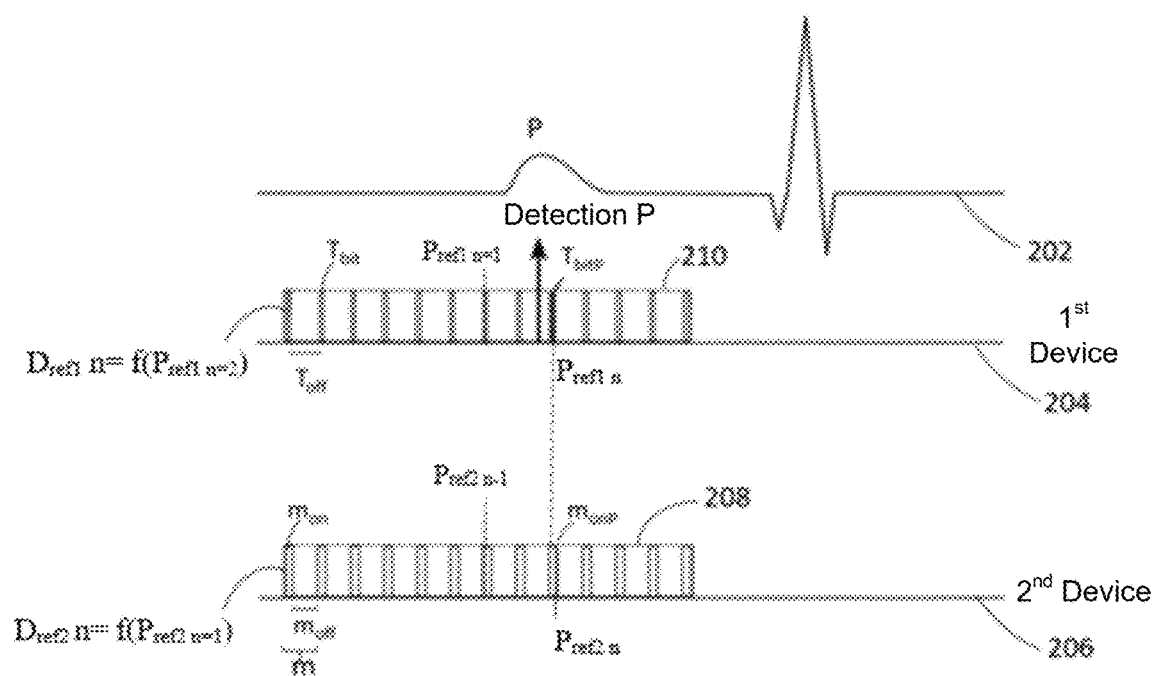
FIG. 6 represents a diagram that schematically illustrates the method of communication according to a second embodiment of the present invention.

FIG. 6 schematically illustrates the operation of the method of communication according to a second embodiment of the present invention.

In a similar manner to FIG. 5, FIG. 6 represents three time axes 202, 204, 206. The unit of the axes 202, 204, 206 is expressed in milliseconds (ms).

An ECG is shown on the time axis 202. The ECG comprises a PQRST complex. The duration of a complete cardiac cycle can be determined as the duration between two successive identical waves.

A synchronization interval 210 of a first device of a multi-device system, as described with reference to FIGS. 1, 3 and 4, is shown on the time axis 204.

A synchronization interval 208 of a second device of a multi-device system, as described with reference to FIGS. 1, 3 and 4, is shown on the time axis 206. This second device may be the leadless autonomous pacemaker 21 configured to be implanted in the right ventricle (RV). The second device may thus be capable of delivering ventricular pacing.

The second device of FIG. 6 is independent of the first implantable medical device and comprises at least one receiving means.

For a cardiac cycle n, the synchronization interval 208 of the second device is determined in the same manner as described for the synchronization interval 108 of the second device at the third cycle of the first embodiment (see FIG. 5). In other words, the start $D_{ref2\ n}$ of the synchronization interval 208 of the second device illustrated in FIG. 6 is a function of the second time marker $P_{ref2\ n-1}$ of the previous cardiac cycle n–1 (which is not represented in FIG. 6).

Likewise, for a cardiac cycle n, the synchronization interval 210 of the first device is determined in the same manner as described for the synchronization interval 110 of the first device at the third cycle of the first embodiment (see FIG. 5). In other words, the start $D_{ref1\ n}$ of the synchronization interval 210 of the first device illustrated in FIG. 6 is a function of the first time marker $P_{ref1\ n-1}$ of the previous cardiac cycle n–1 (which is not shown in FIG. 6).

During the synchronization interval 208, the transmitter means of the first device may transmit pulses of duration $T_{bit}$ spaced apart by rest periods $T_{off}$ as depicted on the time axis 204 of FIG. 6. During the rest periods $T_{off}$, the transmitter means does not send pulses. The durations $T_{bit}$ can be equal to 500 microseconds (μs) and "$T_{off}$" can be equal to 9.5 milliseconds (ms).

Immediately upon detection of a P wave, indicated by "detection P" in FIG. 6, the transmitter means of the first device uses the first available slot defined by $T_{bit}$ to transmit a synchronization signal. Thus, notwithstanding that FIG. 6 represents a plurality of $T_{bit}$ slots, only one slot is used by the transmitter means to send the synchronization signal.

In other words, when the first device detects a P wave, the transmitter of the first device is configured to send a synchronization signal to the first block $T_{bit}$ that follows the detection of the P wave, which is indicated by the block $T_{bit\ P}$ in FIG. 6. The sending of the synchronization signal is marked by the time marker $P_{ref1\ n}$. The time marker $P_{ref1\ n}$ may indicate the start of the sending of the signal or the end of the sending of the signal.

To further reduce power consumption of the second device, in the second communication mode, the receiving means of the second device is activated and then deactivated by the controller at intervals during the synchronization interval 208.

The synchronization interval 208 of the second device thus comprises a plurality of activation time slots "$m_{on}$" and a plurality of deactivation time slots "$m_{off}$". In other words, the synchronization interval 208 comprises a succession of blocks "m", each of which comprises a slot $m_{on}$ and a slot $m_{off}$, as illustrated in FIG. 6 on the time axis 206.

During an activation time slot "$m_{on}$", the receiving means is activated, it is configured to receive a signal, in particular the synchronization signal transmitted by the first device.

During a deactivation time slot "$m_{off}$", the receiving means is deactivated, which is to say it is switched off and does not consume any energy.

In the example of FIG. 6, each activation time slot "$m_{on}$" is of the same duration.

In the example of FIG. 6, each deactivation time slot "$m_{off}$" is of the same duration.

The duration of each slot $m_{on}$ may be of equal duration or shorter than the duration of each slot $m_{off}$.

The synchronization intervals 208, 210 of the cardiac cycle n are synchronized with each other on the basis of the time markers $P_{ref2\ n-1}$ and $P_{ref1\ n-1}$ of the previous cardiac cycle n–1, as explained with reference to FIG. 5.

Moreover, the plurality of predefined activation time slots $m_{on}$ of the second device are synchronized to the plurality of time slots $T_{bit}$ of the first device on the basis of the second time marker $P_{ref2\ n-1}$ and the first time marker $P_{ref1\ n-1}$ of the previous cardiac cycle n–1.

As illustrated in FIG. 6, the synchronization signal is received by the receiver of the second device during the activation slot indicated by "$m_{on\ P}$". The receipt of the signal is marked by the time marker $P_{rep\ n}$.

The duration of an activation time slot $m_{on}$ can represent between 0.3 and 50% of the duration of one deactivation time slot $m_{off}$. The duration of an activation time slot $m_{on}$ depends on the quality of the receiver and the time it needs to detect the synchronization signal. In particular, the duration of an activation time slot $m_{on}$ can represent 5 to 10% of the duration of a deactivation time slot $m_{off}$.

When considering a synchronization interval 208 of about 350 ms and a ratio $m_{on}$=10% of m (m=$m_{on}$+$m_{off}$), it turns out that the improvement of the activation cycle of the receiving means of the second device for synchronization purposes can reduce power consumption by 0.1 to 3.5%. For example, a block m may be equal to a duration of 10 ms, with the block m comprising a slot $m_{on}$ of 1 ms and a slot $m_{off}$ of 9 ms.

In an advantageous variant, the receiving means of the second device is deactivated for the remainder of the given cardiac cycle, once the time marker $P_{ref2\ n}$ has been determined, in order to conserve further power. In the example of FIG. 6, this would translate in the deactivation of the receiving means starting out from block $m_{on\ P}$ until the end of the cardiac cycle n.

Figure 7:
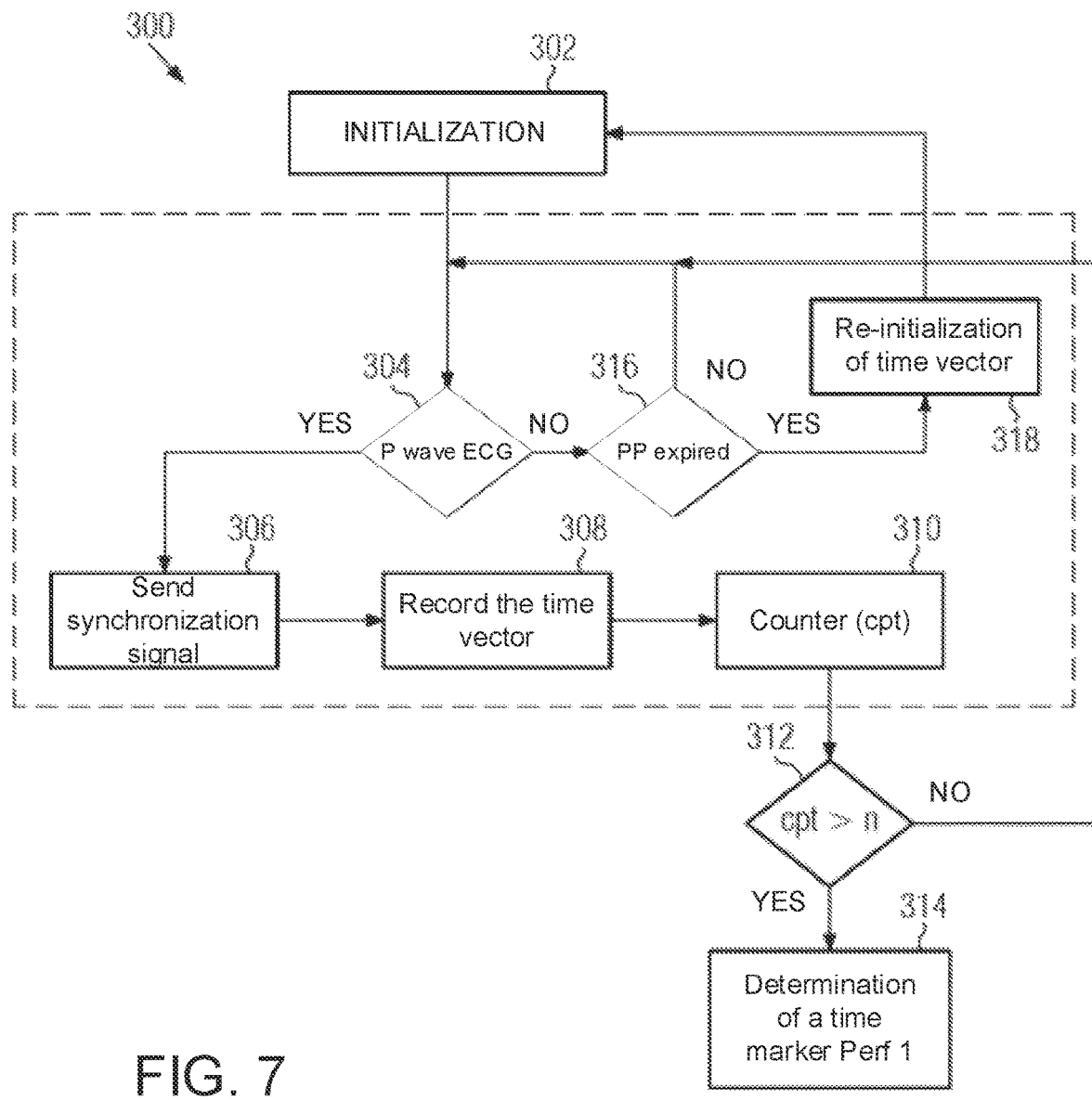
FIG. 7 represents a flowchart that describes initialization steps of the method implemented by a first device.

FIG. 7 illustrates initialization steps of the method implemented by the first device, by means of a flowchart 300. These initialization steps are implemented in an asynchronous manner with respect to the second device. The method steps of the flowchart 300 apply to the embodiments described with reference to FIGS. 5 and 6.

As illustrated by the flowchart of FIG. 7, the initialization 302 includes the detection of a time marker of a cardiac cycle in step 304. This time marker corresponds to the detection of a predefined electrical wave of the PQRST complex. As previously explained, the first device is indeed configured to analyze data that are representative of an ECG.

Preferably, the time marker corresponds to the detection of the P wave which is the first detectable wave of the PQRST complex. The P wave appears when the stimulus (or impulse) propagates to the atrial myocardium, depolarizing the atria.

In the following, reference is thus made to the detection of the P wave, which has been chosen as the predefined electrical wave in the embodiment of FIG. 7, as indicated in step 304 of the flowchart 300. It should be kept in mind that the choice of the P wave is however not limiting, and that another wave of the PQRST complex may be considered, in particular the R-wave.

If a P wave is detected in step 304, a synchronization signal is transmitted in step 306 to the second device.

The synchronization signal thus represents the timing of the detection of the P wave. The synchronization signal for each cardiac cycle enables indication that a depolarization of the atria, in particular of the right atrium, has been detected.

In a step 308, which follows step 306, a time vector characterizing the timing at which the synchronization signal was transmitted in step 306 is saved. The time vector can be saved in a "first in-first out" (FIFO) memory. In other words, a time marker marking the sending of the synchronization signal is determined in step 308.

Then, in a step 310, the time vector is incremented in a counter in such a manner that when a plurality "n" of time markers for n cardiac cycles—and thus as many time vectors—have been incremented in a step 312, they can be compared with each other to define a so-called $P_{ref1}$ reference time marker based on the n time markers.

Thus, in a step 314, the determination of a reference time marker $P_{ref1}$ marking the sending of a synchronization signal is carried out by taking into consideration the timing of the detection of the P wave for a number n of cardiac cycles (for example, by calculating an average over n cardiac cycles), in particular n being greater than or equal to three, provided that the n cardiac cycles are considered regular cardiac cycles. Cardiac cycles are considered regular when the maximum cycle-to-cycle acceleration does not exceed 25%. For example, with an average cardiac cycle (which can be defined by an interval PP) of 1 s, an interval PP of duration greater than or equal to 750 ms is considered stable.

If no P wave is detected in step 304, it is verified in step 316 that the duration of the cardiac cycle has not yet expired. The duration of a cardiac cycle can be determined, for example, by the duration between two successive time markers marking the sending of the signal or two successive P waves. Note that in the initialization phase, a predetermined "initialization" interval PP can be used.

According to the present invention, the duration of a cardiac cycle may also be determined by means of the first device and/or the second device via a detection means, which allows, for example, to obtain the plot of an ECG.

If the duration of the cardiac cycle is not considered to have expired in step 316, then the first device continues to analyze the ECG in step 304.

On the contrary, if the cardiac cycle time is considered to have expired in step 316, the time vector is reset in step 318 and thus returns to the first initialization step 302.

Following the initialization steps of the method, a reference time marker $P_{ref1}$ that is indicative of the timing of the sending of a synchronization signal following the detection of a P wave is thus determined in step 314 of the flowchart 300.

This reference time marker $P_{ref1}$ is, for example, represented in FIGS. 5 and 6.

Figure 8:
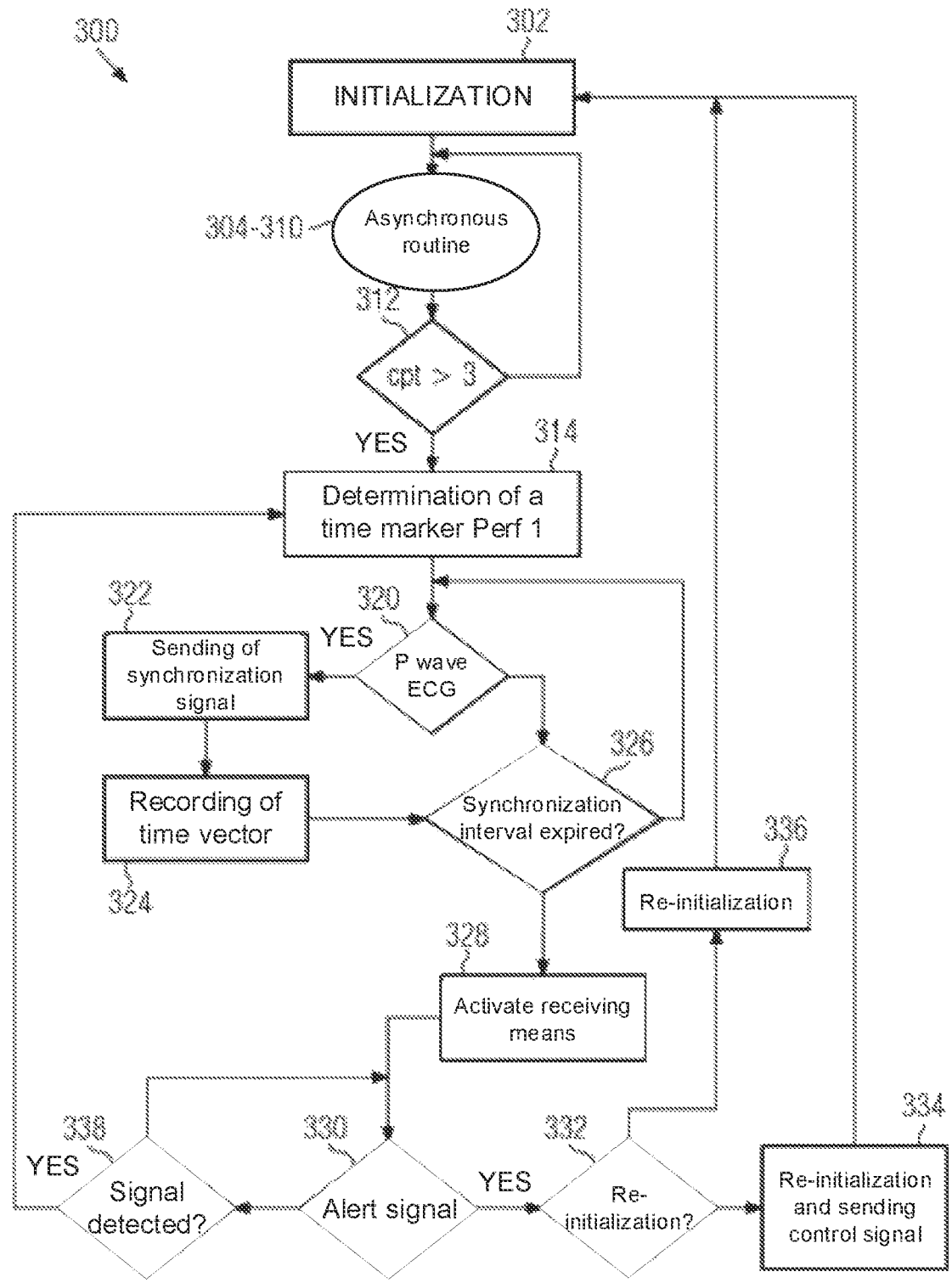
FIG. 8 depicts a flowchart that describes operational steps of the method implemented by the first device.

FIG. 8 illustrates the continuation of the flowchart 300 of FIG. 7, which is to say, of the operational steps of the method that follow step 314, in which step a reference time marker $P_{ref1}$ is determined. Thus, the steps of the method described by means of FIG. 8 apply to the embodiments described with reference to FIGS. 5 and 6.

During the operational steps of the method, a synchronization interval for the first device is used. Such a synchronization interval 110, 210 has already been described in relationship with FIGS. 5 and 6, to which reference is made.

If a P wave for the next cardiac cycle n+1 is detected in step 320, then a corresponding synchronization signal is sent in a step 322 to the second device. The synchronization signal carries physiological information relating to the detection of the PQRST complex and enables the delivery of a synchronized therapy.

In a step 324, which follows the transmission of the synchronization signal of step 322, a time vector characterizing the time at which the synchronization signal was transmitted in step 322 is saved. The time vector can be saved in a FIFO-type memory.

It is then verified in a step 326 whether the synchronization interval 110, 210 for the cardiac cycle n+1 has expired. If this is not the case, the first device continues to be activated and waits for the detection of a P wave for the cardiac cycle n+1 in order to send a synchronization signal.

If a P wave is detected in step 320, a synchronization signal is transmitted in step 322. Then, if it is confirmed in step 326 that the duration of the synchronization interval 110, 210 has expired, then the first device is configured to activate a receiving means of the first device in step 328.

Step 328 is further described below with reference to FIG. 8a.

Figure 8A:
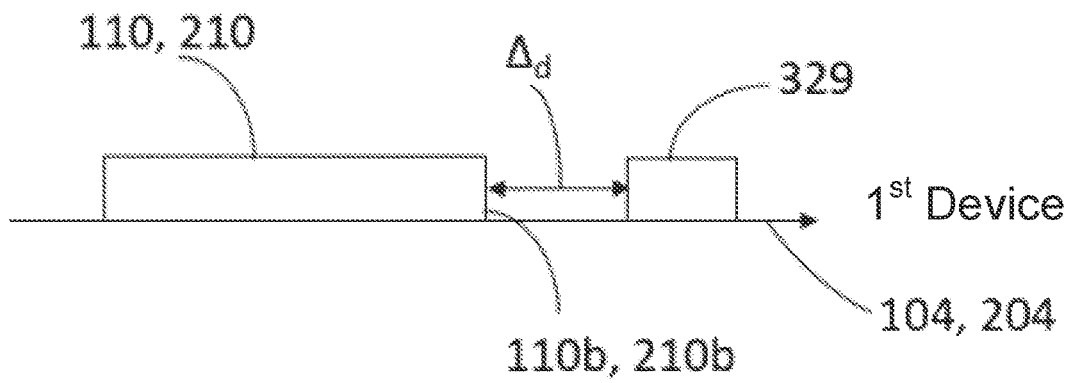
FIG. 8a illustrates one step of the flowchart represented in FIG. 8.

As illustrated in FIG. 8a, the transmitter means of the first device is configured to be activated during a synchronization interval 110, 210. The first device may moreover comprise a receiving means configured to be activated during an interval 329 that is shorter than the synchronization interval 110, 210. The receiving means of the first device may be activated with a predetermined offset $\Delta_d$, starting from the end 110a, 210a of the synchronization interval 110, 210, as illustrated on the time axis 104, 204 of FIG. 8a.

During the interval 329, the receiving means of the first device is activated to detect a possible alert signal transmitted by the second device. The transmission of an alert signal by the second device is further described below with reference to FIGS. 9 and 10.

If, in step 330, the receiving means of the first device receives an alert signal, it is determined in step 332 whether to reset the method and transmit a control signal in order to require delivery of pacing to the right atrium (step 334) or only reset the method without requiring delivery of pacing (step 336).

In the event that no alert signal is detected during the interval 329 in step 338, the first device continues to operate in a near-synchronized manner using the synchronization interval 110, 210 for the wireless communication with the second device.

The flowchart 300 illustrated in FIGS. 7 and 8 thus represents an algorithm implemented by the first device of the multi-device system.

The multi-device system according to the present invention comprises at least one second device, configured to be implanted in the right ventricle, and in which an algorithm is also implemented. The second device is independent of the first device. However, the second device implements an algorithm that is complementary to that of the first device. The algorithm implemented by the second device is hereinafter described by means of a flowchart 400, illustrated in FIGS. 9 and 10.

Figure 9:
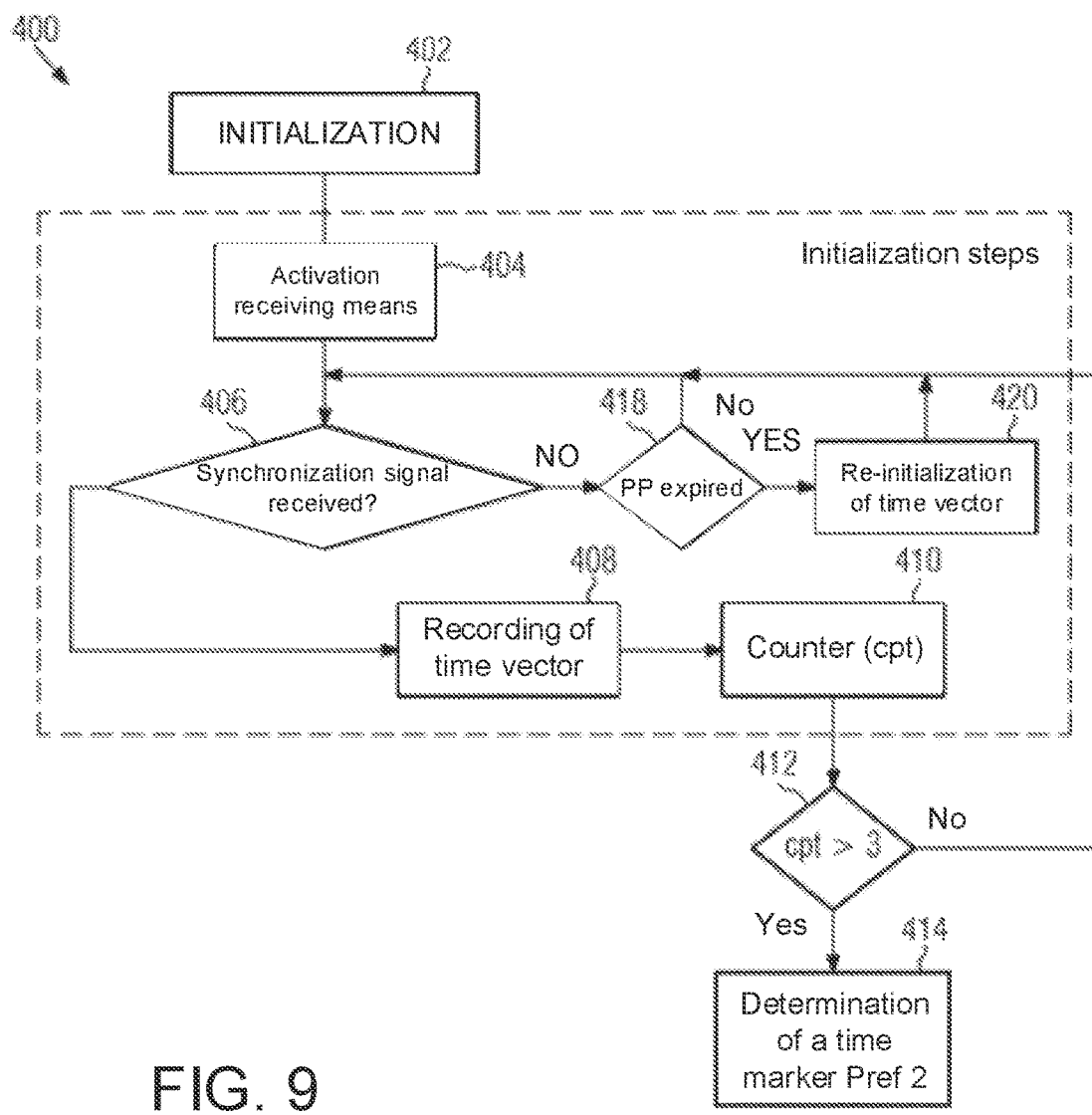
FIG. 9 represents a flowchart that describes initialization steps of the method implemented by a second device.
Figure 10:
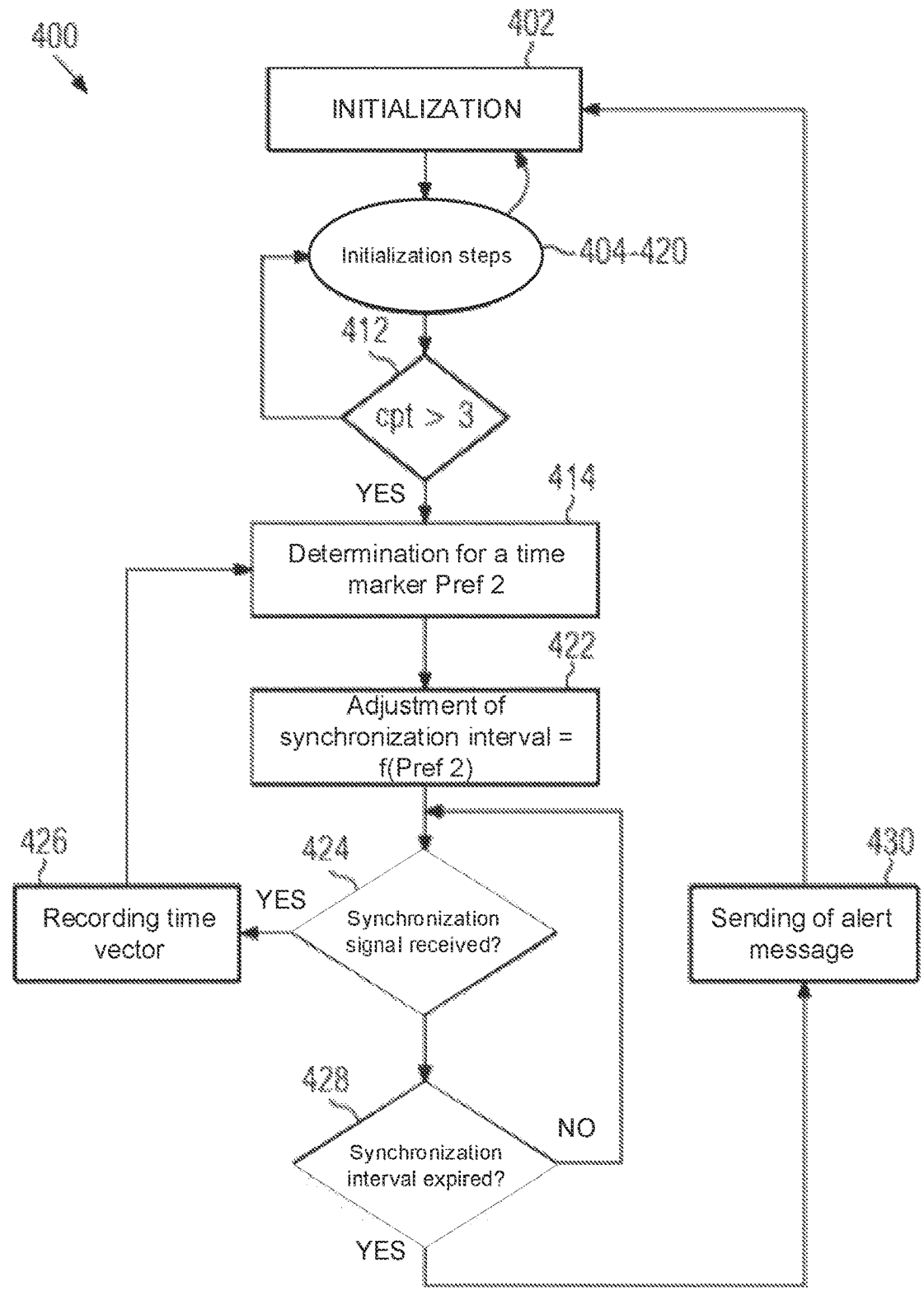
FIG. 10 represents a flowchart that describes operational steps of the method implemented by the second device.

FIGS. 9 and 10 represent a flowchart 400 of the method implemented by the second device.

The flowchart 400 of FIG. 9 represents initialization steps of the method implemented by the second device. These initialization steps are implemented in an asynchronous manner with respect to the first device. The steps of the method of the flowchart 400 can apply to the embodiments described with reference to FIGS. 5 and 6.

During these initialization steps implemented by the second device, the receiving means of the second device is continuously activated since the timing of the receipt of a synchronization signal is not yet estimated.

To begin, as illustrated by the flowchart of FIG. 9, the initialization 402 includes activation of the receiving means of the second device in step 404.

It is analyzed in step 406 whether a synchronization signal is received by the receiving means of the second device.

If a synchronization signal is indeed received, then, in step 408, a time vector characterizing the timing at which the synchronization signal was received in step 406 is saved. The time vector may be saved in a FIFO-type memory.

Then, in step 410, the time vector is incremented in a counter in such a manner that when a plurality n of time vectors for n cardiac cycles—and thus as many as synchronization signals received—have been incremented in step 412, they can be compared with each other in order to define a so-called reference time marker $P_{ref2}$ for the second device.

Thus, in a step 414, the determination of a reference time marker $P_{ref2}$ is carried out by taking into consideration the timing of the receipt of the synchronization signal for a number n of cardiac cycles, wherein, in particular, n is greater than or equal to three, provided that the n cardiac cycles are considered regular cardiac cycles. Cardiac cycles are considered regular when the maximum cycle-to-cycle acceleration does not exceed 25%. For example, with an average cardiac cycle (which can be defined by an interval PP) of 1 s, an interval PP of duration greater than or equal to 750 ms is considered stable. The reference time marker $P_{ref2}$ can, in particular, be determined by carrying out an average of the timings of the receipt of the synchronization signal for a number n of cardiac cycles.

If no synchronization signal is received in step 406, it is verified in a step 418 that the duration of the cardiac cycle that is considered has not yet expired. The duration of a cardiac cycle may, for example, be determined by the duration between two successive P waves.

Thus, the second device may be configured to estimate the duration of a cardiac cycle by means of timing information contained in two successively received synchronization signals.

In one variant, the second device may comprise a detection means, which may, for example, permit one to obtain an ECG plotting and from the plotting derive a cardiac cycle duration. If the duration of the cardiac cycle is not considered to have expired in step 418, then the second device continues to wait for receipt of a synchronization signal in step 406.

On the contrary, if the cardiac cycle time is considered to have expired in step 418, the time vector is reset in step 420 and thus returns to step 406.

Following the initialization steps of the method, a reference time marker $P_{ref2}$, that is indicative of the timing of the receipt of a synchronization signal and related to the detection of a P wave in the atria, is thus determined in step 414 of the flowchart 400.

Such a reference time marker $P_{ref2}$ is, for example, represented on the time axis 106, 206 of FIGS. 5 and 6.

FIG. 10 illustrates the continuation of the flowchart 400 of FIG. 9, which is to say, of the operational steps of the method that follow step 414 in which the reference time marker $P_{ref2}$ is determined. According to the second embodiment, during the operational steps of the method, in particular from step 422 onwards described below, the receiving means of the second device is no longer activated continuously but rather by intervals during the synchronization interval 208. Reference is made to the description of FIG. 6 for the activation of the receiving means in intervals during blocks $m_{on}$ of the synchronization interval 208.

As illustrated by FIG. 10, in a step 422 which follows step 414, the second device updates and adjusts the synchronization interval 208 relative to the value of the reference time marker $P_{ref2}$ determined in step 414. The synchronization interval 208 of a cardiac cycle n is adjusted as a function of the value of the reference time marker $P_{ref2}$ determined at the previous cardiac cycle n−1 or as a function of the average of the values of the reference time marker $P_{ref2}$ determined from a plurality of previous cardiac cycles.

In a step 424, the receiving means is activated over the synchronization interval 208 during a plurality of activation time slots $m_{on}$, as illustrated in FIG. 6.

It is analyzed in step 424 whether a synchronization signal transmitted by the first device, is received by the receiving means of the second device.

If a synchronization signal is indeed received, then, in step 426, a time vector characterizing the timing at which the synchronization signal was received is saved. The time vector can be saved in a memory of the first in-first out (FIFO) type.

The time vector is used in step 414 to update the timing of the receipt of the synchronization signal, which is to say, the reference time marker $P_{ref2}$ that will be used for the next cardiac cycle. The reference time marker $P_{ref2}$ is thus updated beat-by-beat since it is calculated on the basis of the reference time markers $P_{ref2}$ of the previous beats, for example on the basis of the two previous cardiac cycles n−2 and n−1 that preceded the cardiac cycle n under consideration.

If no synchronization signal is received in step 424, it is verified in a step 428 that the duration of the synchronization interval 208 has not yet expired.

If the duration of the synchronization interval 208 has not yet expired in step 428, then the second device continues to wait for receipt of a synchronization signal in step 424.

On the contrary, if the duration of the synchronization interval 208 has expired in step 428 without a signalization signal being received, the second device is configured to send an alert signal in step 430. To do so, the second device further comprises a transmitter means.

Note that the second device does not know the cause of the failure to receive a signaling signal. It may be a communication failure, or rather that a P wave was not detected by the first device. In either case, the second device sends an alert signal in step 430.

Step 430 is further described hereinafter with reference to FIG. 10a.

In step 430, the second device is configured to activate a transmitter means. As shown in FIG. 10a, the transmitter means of the second device is configured to be activated during an interval 431 that is shorter than the synchronization interval 208.

Figure 10A:
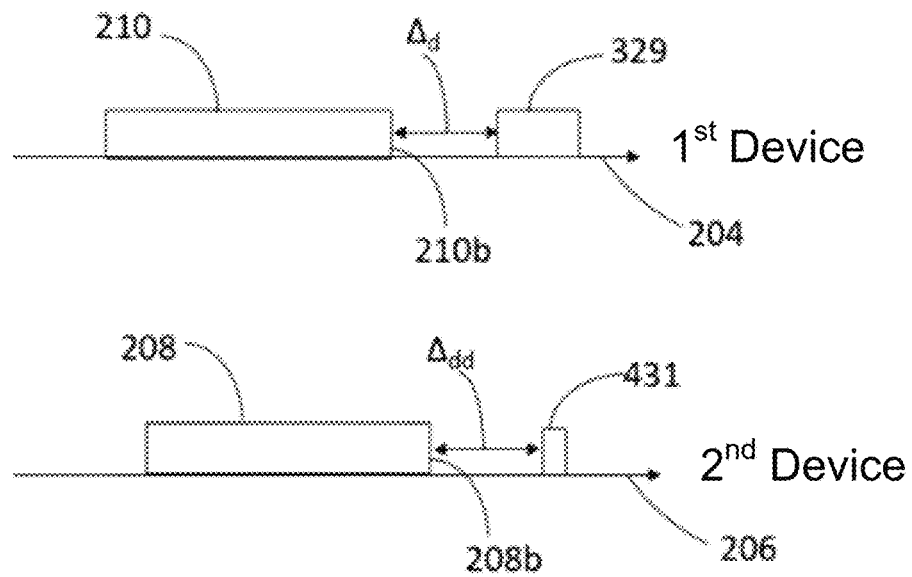
FIG. 10a illustrates one step of the flowchart represented in FIG. 10.

The alert signal may be sent with a predetermined offset $\Delta_{dd}$ after the end 208b of the synchronization interval 208 as represented on the time axis 206 of FIG. 10a.

Thus, during the interval 431, the transmitter means of the second device is activated to send an alert signal to the first device. The activation interval 431 of the transmitter means of the second device is shorter than the activation interval 329 of the receiving means of the first device.

The activation interval 431 of the transmitter means of the second device can be used for two purposes: both to inform the first device of the failure of the communication (due to the lack of receipt of a synchronization signal)—the first device knowing that its transmitter means has indeed sent a synchronization signal, or to require an artificial and local pacing of the right atrium.

The method of communication of the present invention allows synchronization of the therapy delivered by the multi-device system and enables the saving of a considerable amount of energy.

However, patients fitted with such a multi-device system may suffer from episodes in which atrial activity becomes rapid and irregular, known as supraventricular tachyarrhythmia. In this case, the therapy delivered to the ventricle must be independent of the atrial activity.

Moreover, a patient suffering from atrial arrhythmia needs to temporarily uncouple the dual-chamber (or triple-chamber) therapy in order to desynchronize the ventricle (or ventricles) from the atrium.

Figure 11:
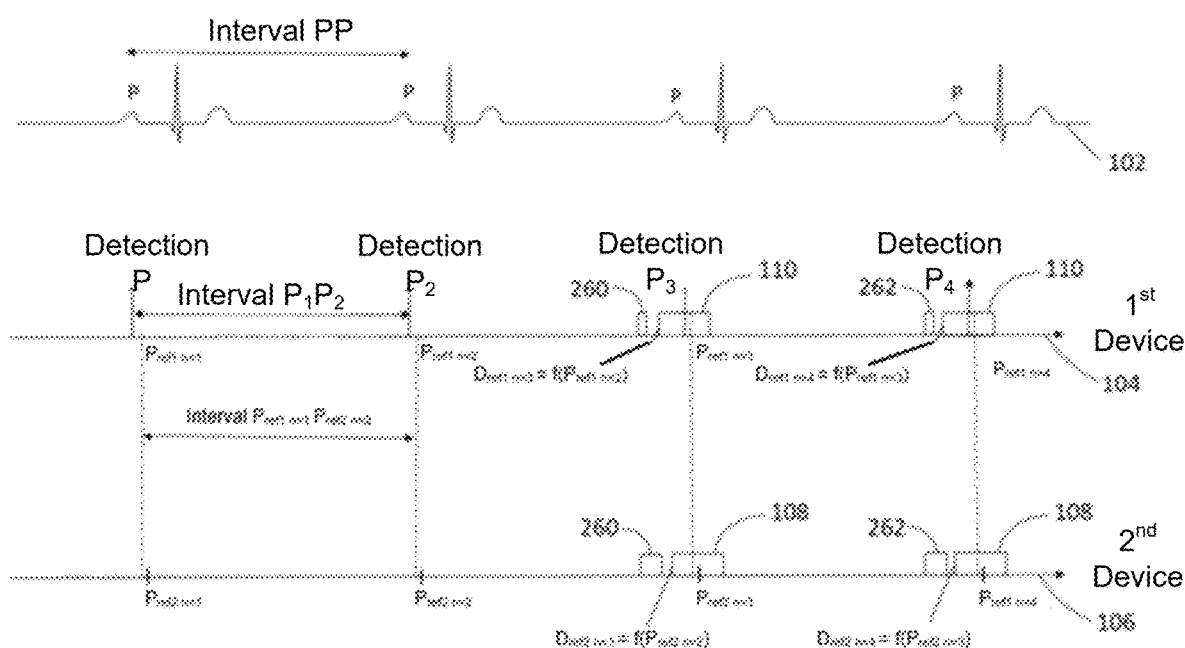
FIG. 11 represents another variant of the first and of the second embodiments of the present invention.

FIG. 11 illustrates an alternative variant of the first and second embodiments advantageously adapted to the case of the aforementioned cardiac rhythm disorders.

FIG. 11 is based on diagram 100 of FIG. 5, to which a so-called start interval 260, 262 that precedes the synchronization intervals 208, 210 for each of the first device and the second device is added on each of the time axes 104, 106.

During the start-up interval 260, the transmitter means of the first device is configured to send a start authorization signal to the receiving means of the second device.

Thus, during the start-up interval 262, the receiving means of the second device is configured to receive the start-up authorization signal transmitted by the second device.

The start-up intervals 260, 262 allow or disallow communication between the first device and the second device.

It is likewise possible that the first device waits for a receipt acknowledgement signal that is sent by a transmitter means of the second device in order to ensure that the information was correctly received by the second device.

This prevents that energy is unnecessarily dissipated to activate the receiving means of the second device, by way of example, during cardiac arrhythmia episodes.

The start-up intervals 260, 262 may also more simply provide a "switch" function, so that they can be switched from a single-chamber mode of operation (which is to say, a mode where the devices are not synchronized) to a dual-chamber mode of operation (which requires the devices to be synchronized).

The wireless method of communication and the multi-device system configured to implement said method of the present invention allow to adjust and adapt communication windows—which correspond to the synchronization intervals—to the electrophysiological rhythm of the patient. Indeed, each device of the system is capable of determining a time marker associated with the detection of P waves (or any other wave of the PRQST complex) and of rearranging the communication window as a function of the time marker that is thus determined for each cardiac cycle.

The invention claimed is:

1. A method of communication in a system comprising a plurality of implantable medical devices, wherein a first device comprises at least one means for detection of a signal that is representative of atrial activity, a transmitter, and a controller configured to analyze the signal that is representative of the atrial activity, and a second device, that is independent of the first device, comprising at least one receiver and a controller, wherein the method comprises:
synchronizing the first device with the second device, the synchronizing including sending a synchronization signal from the transmitter of the first device to the second device, the synchronization signal being sent following an identification, by the controller of the first device, of a predefined electrical wave of the PQRS complex of the signal representative of the atrial activity;
determining the duration of a cardiac cycle;
determining a synchronization interval of the second device, the duration of the synchronization interval of the second device determined as a function of the duration of the cardiac cycle, the synchronization interval of the second device being shorter than the duration of the cardiac cycle, and the start of the synchronization interval of the second device is determined as a function of the synchronization signal;
activating the receiver of the second device during the synchronization interval of the second device, wherein the receiver of the second device is deactivated outside of the synchronization interval of the second device by the controller of the second device.

2. The method of claim 1, wherein sending the synchronization signal by the transmitter of the first device includes a first time marker; and receiving the synchronization signal by the receiver of the second device includes a second time marker, where a synchronization interval of the first device for a subsequent cardiac cycle is determined as a function of the first time marker, and the synchronization interval of the second device for a subsequent cardiac cycle is determined as a function of the second time marker.

3. The method of claim 2, wherein during the synchronization interval of the second device:
the receiver of the second device is activated during a plurality of predefined activation time slots and is deactivated during a plurality of predefined deactivation time slots, where the plurality of predefined activation time slots of the second device is distributed over the synchronization interval of the second device to be synchronized with signal pulse slots of the first device as a function of the first time marker and the second time marker.

4. The method of claim 3, wherein the transmitter of the first device is configured to send a single synchronization signal per cardiac cycle.

5. The method of claim 4, wherein:
each of the predefined activation time slots is the same duration,
each of the predefined deactivation time slots is the same duration, and
each of the predefined activation time slots and the predefined deactivation time slots alternatingly follow each other in the synchronization interval of the second device.

6. The method of claim 5, wherein the duration of an activation time slot is shorter than or equal to the duration of a deactivation time slot.

7. The method of claim 6, wherein the duration of an activation time slot represents between 0.3% and 50% of the duration of a deactivation time slot, in particular 5% to 10%.

8. The method of claim 3, wherein the duration of a pulse during which the transmitter of the first device is configured to transmit a synchronization signal corresponding to 25% to 80% of the duration of an activation time slot, in particular 50%.

9. The method of claim 2, wherein the first time marker marks the start or end of sending of the synchronization signal or a predetermined time during the sending of the synchronization signal.

10. The method of claim 1, wherein the predefined electrical wave detected by the controller of the first device corresponds to a P wave of the PQRS complex.

11. The method of claim 1, wherein the predefined electrical wave is detected by means of the controller of the first device by analysis of at least one of an electrogram, an electrocardiogram, data measured by an accelerometer, data measured by cardiography impedance or data measured by an acoustic sensor.

* * * * *